(12) United States Patent
Akcay et al.

(10) Patent No.: US 12,274,840 B2
(45) Date of Patent: *Apr. 15, 2025

(54) SAFETY CATHETER WITH PASSIVE RELEASE

(71) Applicant: ICU MEDICAL, INC., Plymouth, MN (US)

(72) Inventors: Gursel Akcay, Madison, CT (US); Harsh D Chheda, Cheshire, CT (US); David J Goral, Brookfield, CT (US); Thomas T Koehler, Pelzer, SC (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,203

(22) Filed: Feb. 8, 2024

(65) Prior Publication Data

US 2024/0181220 A1 Jun. 6, 2024

Related U.S. Application Data

(63) Continuation of application No. 18/096,149, filed on Jan. 12, 2023, now Pat. No. 11,931,533, which is a continuation of application No. 16/717,063, filed on Dec. 17, 2019, now Pat. No. 11,590,324, which is a continuation of application No. 16/065,578, filed as application No. PCT/US2018/023550 on Mar. 21, 2018, now Pat. No. 10,543,341.

(60) Provisional application No. 62/475,428, filed on Mar. 23, 2017.

(51) Int. Cl.
*A61M 25/06* (2006.01)

(52) U.S. Cl.
CPC .... *A61M 25/0618* (2013.01); *A61M 25/0606* (2013.01); *A61M 25/0693* (2013.01)

(58) Field of Classification Search
CPC .......... A61M 25/0618; A61M 25/0606; A61M 25/0693
USPC ..................................................... 604/164.08
See application file for complete search history.

(56) References Cited

U.S. PATENT DOCUMENTS

| | | | |
|---|---|---|---|
| 6,595,954 B1 | 7/2003 | Luther et al. | |
| 8,647,301 B2 | 11/2014 | Bialecki et al. | |
| 2009/0312711 A1* | 12/2009 | Brimhall | A61M 25/0618 604/164.08 |
| 2015/0290430 A1* | 10/2015 | Koehler | A61M 25/0618 604/164.08 |
| 2016/0015941 A1 | 1/2016 | Tanabe et al. | |

OTHER PUBLICATIONS

EUIPO: Notice of Intention to Grant dated Dec. 4, 2020 in U.S. Appl. No. 16/065,578 (document filed in parent case U.S. Appl. No. 16/065,578).

(Continued)

*Primary Examiner* — Phillip A Gray
(74) *Attorney, Agent, or Firm* — Louis Woo (57) ABSTRACT

A safety intravenous catheter that includes a passive release feature. The catheter assembly includes ready, safe, and released positions. In the release position, a retainer being in a proximal retainer position relative to a collar enables release of the catheter hub from the catheter insertion device. The sharp tip of the insertion needle remains inaccessible in the release position in order to prevent unwanted needle sticks.

19 Claims, 6 Drawing Sheets

(56) References Cited

OTHER PUBLICATIONS

International Search Report & Written Opinion dated Jun. 1, 2018 in PCT/US2018/023550 (document filed in parent case U.S. Appl. No. 16/065,578).
International Report on Patentability dated Oct. 3, 2019 in PCT application No. PCT/US2018/023550 (document filed in parent case U.S. Appl. No. 16/065,578).
EUIPO Extended European Search Report dated Jan. 20, 2020 in EP application No. 18771336.7.
USPTO Notice of Allowance dated Oct. 7, 2019 in U.S. Appl. No. 16/065,578.
USPTO Notice of Allowance dated Jan. 2, 2024 in U.S. Appl. No. 18/096,149.

\* cited by examiner

SAFETY CATHETER WITH PASSIVE RELEASE

CROSS-REFERENCE TO RELATED APPLICATIONS

This application is a continuation of U.S. application Ser. No. 18/096,149 filed Jan. 12, 2023 entitled "Safety Catheter with Passive Release.". The '149 application is a divisional of U.S. application Ser. No. 16/717,063 filed Dec. 17, 2019 entitled "Safety Catheter with Passive Release.". The '063 application in turn is a continuation of U.S. application Ser. No. 16/065,578 filed Jun. 22, 2018, entitled "Safety Catheter with Passive Release." The '578 application is the National Stage Application of PCT/US2018/023550 filed Mar. 21, 2018, entitled "Safety Catheter with Passive Release." The '550 PCT claims priority to U.S. Provisional Application Ser. No. 62/475,428 filed Mar. 23, 2017 entitled "Safety Catheter with Passive Release." Each of these references is incorporated herein by reference in their entirety for all purposes.

FIELD OF INVENTION

The present disclosure relates to a safety intravenous (IV) catheter and more particularly to a safety IV catheter that includes a passive release feature.

BACKGROUND OF INVENTION

Safety catheter assemblies typically include a catheter hub assembly and a catheter insertion device having an insertion needle. The catheter hub of the catheter hub assembly is assembled to the catheter insertion device (or insertion needle assembly) in a ready for use configuration with a catheter tube of the catheter hub positioned over the insertion needle and a sharp tip of the insertion needle protruding from a distal end of the catheter. A needle sheath may be positioned over the sharp tip of the insertion needle to prevent unwanted needle sticks prior to the safety catheter assembly being used. The overall safety catheter assembly, including the catheter hub assembly, catheter insertion device, and needle sheath, may be provided for use in a sterilized and assembled state, contained within a sealed package. One example of such a safety catheter assembly includes the JELCO INTUITIV (Trademark) safety catheter assembly marketed by Smiths Medical ASD, Inc. of Plymouth, Minn., as described in U.S. Pat. No. 8,257,322.

To insert the catheter into the vein of a subject, a clinician first removes the safety catheter assembly from the packaging. The needle sheath is removed to expose the sharp tip of the insertion needle that is protruding from the distal end of the catheter. The clinician punctures an identified site of a subject with the sharp needle tip and urges the insertion needle forward until the needle tip enters the vein of the subject. An initial amount of blood may pass through a lumen of the needle, entering the catheter and/or catheter insertion device where the clinician may view the "flashback" of the blood to confirm entry into the vein. The catheter may then be moved distally over the needle to thread the tube of the catheter into position in the vein of the subject. The needle may be held stationary during catheter threading. With the catheter positioned as desired, the clinician withdraws the needle by pulling the catheter insertion device proximally away from the subject while holding the catheter hub assembly generally stationary with respect to the subject. The insertion needle is pulled proximally until the needle and catheter insertion device are separated from the catheter hub. The clinician may dispose of the catheter insertion device in a sharps container, after the insertion device is separated from the catheter.

DETAILED DESCRIPTION OF INVENTION

Safety catheter assemblies, according to various example embodiments disclosed herein, may be positioned during use in a ready for use position, a safe and engaged position, and a safe and released position. In the ready for use (referred to herein as the "ready position"), the catheter hub assembly is assembled to the catheter insertion device with the sharp tip of the insertion needle protruding from a distal end of the catheter tube and the catheter hub secured to the catheter insertion device in a manner that prevents the catheter hub assembly and the catheter insertion device from being removed from each other. In the safe and engaged position (referred to herein as the "safe position") the sharp tip of the insertion needle is positioned in a tip protector of the catheter insertion device in order to prevent access to the needle that might otherwise result in unwanted needle sticks. The catheter hub assembly remains secured to the catheter insertion device when in the safe and engaged position. In the safe and released position (referred to herein as the "release position") the catheter hub is disengaged from the catheter insertion device so that the insertion device may be separated from the catheter hub assembly and be disposed of in a safe manner. The sharp tip of the insertion needle remains inaccessible in the release position to prevent unwanted needle sticks.

Turn now to the figures. FIGS. 1a to 3d show an example embodiment of a safety catheter assembly 100 that includes a catheter hub assembly 200, an insertion needle assembly 300, and a needle tip protector assembly 400. The catheter hub assembly 200, insertion needle assembly 300, and needle tip protector assembly 400 are shown in each of the ready position (FIGS. 1a, 2a, and 3a), the safe position (FIGS. 1b, 2b, and 3b), and the release position (FIGS. 1c, 2c, 3c, and 3d), according to one example embodiment. FIGS. 1a-1c and 2a-2c show the safety catheter assembly 100 in respective distal and proximal views. FIGS. 3a-3d are cross sectional views of a substantial portion of the safety catheter assembly.

The catheter hub assembly 200 includes a catheter hub 202 and a catheter tube, or simply catheter 204 that cooperate to provide a fluid pathway between the vein of a subject and other IV fluid components, such as an IV fluid supply. The catheter 204 includes a distal end, a proximal end, and a lumen extending therebetween. The proximal end of the catheter 204 is connected to a distal portion of the catheter hub 202. The proximal end 206 of the catheter hub is constructed and arranged to connect to other IV fluid components and may be designed in accordance with ISO standards. In the illustrated example embodiment, the proximal end of the catheter hub includes luer lugs, although other constructions are also contemplated.

The insertion needle assembly 300 includes an insertion needle 302 having a sharp distal tip 304 that may create an entry passageway into the vein of a subject, as the needle slidably extends through the catheter with its distal tip extending beyond the distal end of the catheter when the catheter assembly is in the ready to use position. The insertion needle extends from the sharp distal tip 304 to a proximal portion that is connected to a needle hub 306, and defines an internal lumen that extends therebetween. The proximal portion of the insertion needle is connected to and in fluid communication with the needle hub 306. The needle hub, in turn, is connected to the flash plug 308 to allow blood to flow from the needle tip 304 to the flash plug. The flash plug 308 may include a microporous barrier that permits the escape of air but prevents the escape of fluid. The body of the insertion needle may include a transition or bump 310 proximal the sharp distal tip that interacts with the needle tip protector to move the safety catheter assembly between the ready, safe, and released positions.

The illustrated example embodiment also includes a needle tip protector 400. The needle tip protector 400 includes an inner member 402, an outer member 404, a retainer 406, and a collar 408, each of which is shown separately in FIGS. 5 to 8. The inner member 402 and the outer member 404 of the needle tip protector 400 cooperate to prevent access to the needle tip 304 in the safe and released positions. Additionally, the retainer 406 and the collar 408 cooperate to secure the catheter hub assembly 200 to the needle tip protector 400 in each of the ready and safe positions, while enabling the needle tip protector 400 to be released from the catheter hub 202 in the release position.

The transition or bump 310 on the body of the needle 302 acts to move the needle tip protector 400 between the ready, safe, and release positions and may also prevent separation of the insertion needle assembly 300 from the tip protector assembly 400. The inner member 402 of the tip protector 404 includes distal arms 410, a proximal base 412, and a bump washer 414. The bump washer 414 defines a proximal opening 418 that allows passage of the needle 302 and a proximal needle stop 416 that prevents bump 310 from passing. When insertion needle 302 is pulled proximally between the ready and safe positions, the proximal needle stop 416 would prevent the transition 310 from passing through the proximal opening 418, thus preventing the tip protector 400 from separating from the needle assembly 300.

In the illustrated embodiment, the proximal needle stop 416 is formed in a bump washer 414 that is assembled to the proximal end of the inner member 402. The bump washer 414 is shaped generally like a traditional washer with the inclusion of a distally extending arm 420 that facilitates connection to other portions of the inner member. The bump washer may be made of a rigid material, such as a metal or plastic that resists deformation when contacted by the transition of the insertion needle. It is to be appreciated that proximal stops, according to alternate example embodiments, may be formed directly in the retainer or in different types of bump washers, such as bump washers that lack a distally extending tab or that are made of materials other than metal.

The transition 310 may be located on the needle 302 so that the needle tip 304 is positioned within the inner member 402 of the tip protector 400 when the transition contacts the proximal stop 416, such that access to the needle tip may be prevented. This may generally be accomplished by locating the transition 310 a distance from the needle tip 304 that is less than the distance between the proximal stop 416 and the distal end 422 of the inner member 402. According to some embodiments, the distance between the transition and the needle tip may be smaller than a distance between the proximal stop and a distal stop on the inner member. It is to be appreciated, however, that other configurations are possible, including embodiments where the transition is located on the needle such that the needle tip is positioned internally to the outer member or another component of the tip protector.

Figures 1A, 1B, 1C:
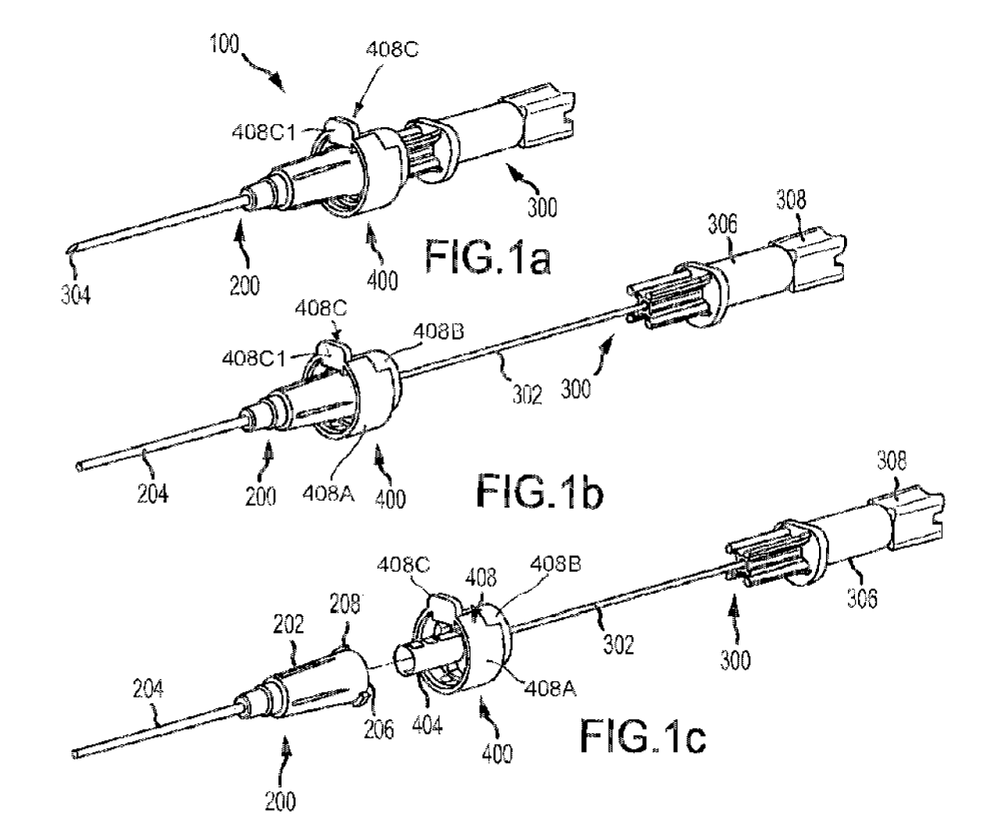
FIGS. 1a-1c are perspective views, taken from a distal vantage, of an example embodiment of a safety catheter assembly in each of a ready position (FIG. 1a), a safe position (FIG. 1b) and a release position (FIG. 1c).
Figure 2A:
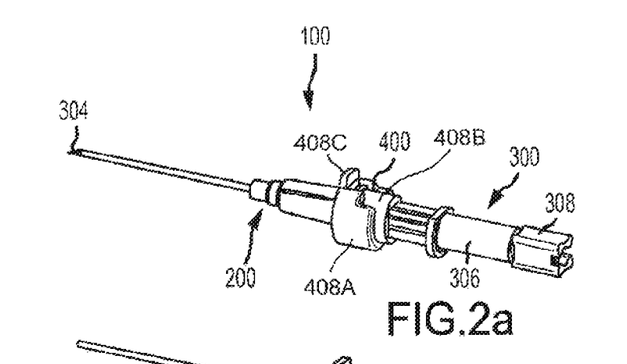
FIGS. 2a-2c are perspective views, taken from a proximal vantage, of the safety catheter assembly of FIGS. 1a-1c in each of a ready position (FIG. 2a), a safe position (FIG. 2b) and a release position (FIG. 2c).
Figure 2B:
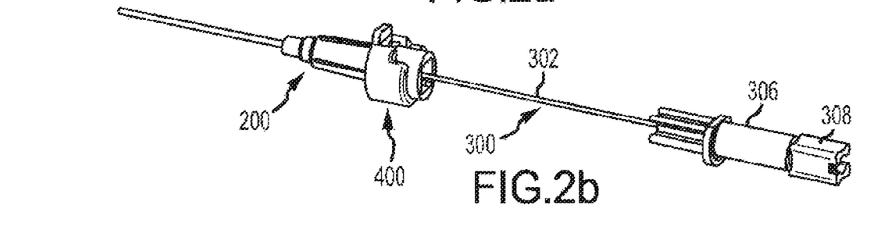
Figure 2C:
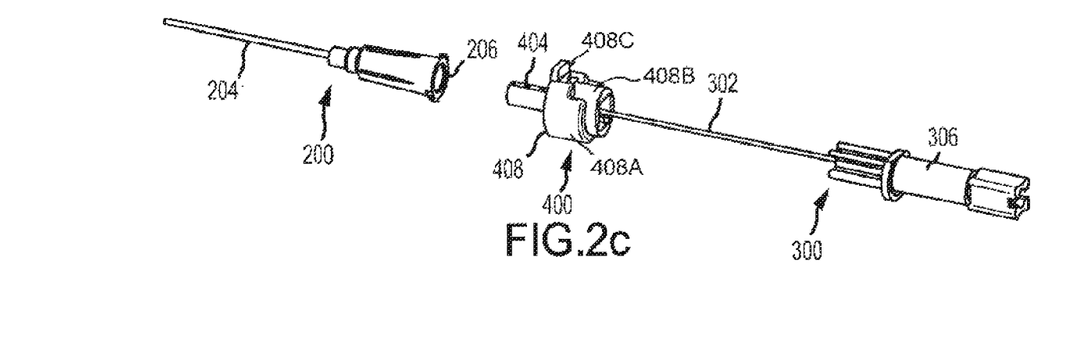
Figure 3A:
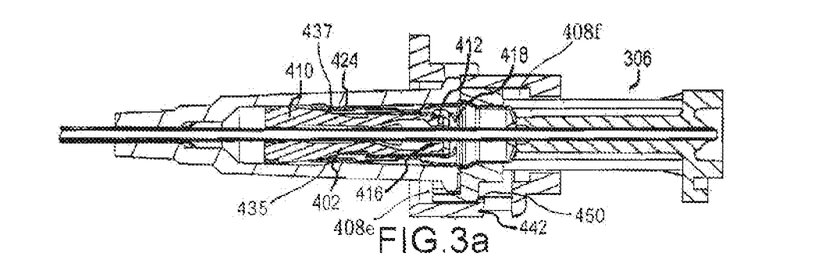
FIGS. 3a-3d are cross section views of the safety catheter assembly of FIGS. 1a-2c in each of a ready position (FIG. 3a), a safe position (FIG. 3b) and a release position (FIGS. 3c and 3d).
Figure 3B:
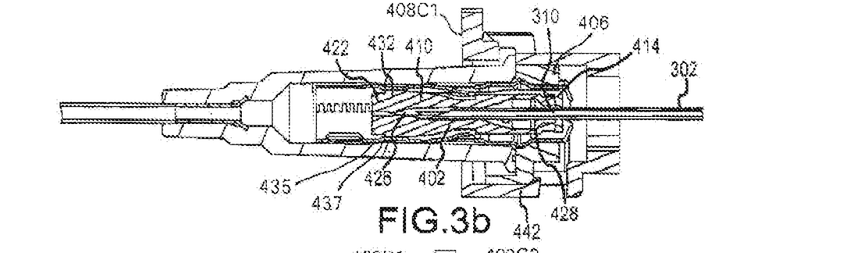

Further proximal movement of the insertion needle 302, once the transition 310 is in contact with the proximal stop 416, causes the inner member 402 to move proximally relative to the outer member 404 from a distal inner member position to a proximal inner member position, as may be seen in the progression of movement between FIGS. 3a and 3b. Movement of the inner member 402 within the outer member 404 causes arms 410 of the inner member to move into a restriction 424 of the outer member. Interaction between the arms 410 and the outer member 424 urges the arms toward one another, causes the arms to form a distal needle stop 426 in the passageway previously occupied by the insertion needle 302. The distal needle stop 426 prevents distal movement of the needle from outside of the interior of the inner member, and thus protects clinicians and others from the sharp needle tip.

The arms of the inner member may include protrusions or ribs that engage one another to form the distal needle stop when the inner member is in the proximal inner member position, such as when the tip protector assembly is in either of the safe or release positions. These or other features of the arms may contact one another, fully occupying the needle passageway to form the distal needle stop, as shown in FIG. 3b. It is to be appreciated, however, that other embodiments may lack such fingers or ribs. It is also to be appreciated that the distal needle stop may not fully occupy the needle passageway when in the safe position, according to alternate embodiments. In one such alternate embodiment, the arms of the inner member are urged toward one another to form a distal needle stop that restricts passage of the sharp needle tip without fully occupying the needle passageway.

The distal arms 410 of the inner member may be biased in the radially outward direction, away from one another. Such a bias may promote separation of the distal arms 410 from one another and thus from the insertion needle 302 prior to the needle reaching the safe position. Such separation may minimize friction between the insertion needle 302 and inner member 402, promoting easy movement of the insertion needle from the ready position to the safe position. According to some embodiments, the inner member is made of a resilient rubber or plastic material.

The distal arms 410 may include a hinge area 428 near a connection to the proximal base 412 and an enlarged distal portion 430. The hinge area may promote flexing of the distal arms between the ready position and the safe position. The enlarged distal portions 430 may be shaped and sized to form the distal needle stop 426 when moved inwards or toward one another by the restriction 424 of the outer member. In the illustrated embodiment, the distal portion of at least one of the arms includes a ramp structure 432 that interacts with the outer member 404 to urge the arm inward 410, toward the needle passageway, as the inner member is pulled proximally by movement of the insertion needle.

The inner member includes a safe position lock 434 that prevents distal movement of the inner member, once in the inner member proximal position relative to the outer member. In the illustrated example embodiment, the lock 434 includes a distally facing inner member lock surface 436 that interacts with an inwardly biased tab 438 of the outer member 404. Proximal movement of the inner member 402 brings the lock surface into engagement with a proximally facing lock surface of the tab 438. Once engaged, the lock surfaces 436 of the inner member 402 and the tab 438 prevent emergence of the needle tip 304 by preventing the inner member 402 from returning to the distal inner member position. It is to be appreciated that the safe position lock shown in the illustrated example embodiment is but one type of lock and that others are also contemplated.

As may be seen in FIGS. 3a and 3b, in each of the ready and safe positions the catheter hub assembly 200 is secured to the needle tip protector assembly 400 in a manner that prevents separation, with the retainer 406 in a distal retainer position relative to the collar 408. This is accomplished by various engagement features in the needle tip protector assembly 400 that secure the catheter hub assembly 200 to the needle tip protector assembly 400 until the needle tip protector assembly 400 is in the release position. In the illustrated embodiment, external engagement features are located on the collar and the retainer. The outer member 404 of the needle tip protector may additionally provide internal engagement features that help to secure the catheter hub assembly 200 to the needle tip protector assembly 400.

As shown in FIGS. 1a-1c to 4a-4c, collar 408 has a distal portion 408a and a proximal portion 408b. Collar distal portion 408a forms a chamber 408e that has a larger circumferential dimension than a chamber 408f formed at collar proximal portion 408b. Distal chamber 408e has a larger circumferential dimension than proximal chamber 408f. A notch 440 at the distal open end or formed along the inner wall in distal chamber 408e is configured to receive at least one luer lug 208 of the catheter hub 202. The notch 440 engages the luer lug to prevent the luer lug and thus the catheter hub 202 from moving distally away from the needle tip protector assembly 400. Contact between the notch and the luer lug of the catheter hub may also prevent the catheter hub assembly 200 from moving laterally away from the needle tip protector assembly 400. As further shown in FIGS. 1a-1c to 4a-4c, the distal portion 408a of collar 408 has an upright 408c that extends upwardly from the top of the distal portion 408a. Upright 408a has a distal front surface 408c1 that is flush with the distal end 408d of distal portion 408a of collar 408 and a proximal back surface 408c2 onto which a clinician may push against.

External engagement features are provided by the retainer 406. The retainer 406 includes a base 406a having a through bore 406b for receiving the proximal end portion 452 of the outer member 404 of the needle tip protector and a distal extension 406c that has a lateral wall 406d. The internal wall surface 406d1 of lateral wall 406d forms a pocket or internal cavity 406e adapted to receive the proximal end 206 of the catheter hub 202. Inner portions of the collar 408 of the needle tip protector assembly 400 engage corresponding outer surfaces of the catheter hub to secure the catheter hub assembly 200 to the needle tip protector assembly 400.

The outer member of the needle tip protector assembly may contact the interior of the catheter hub to provide an interior engagement. As shown in FIGS. 3a-3d, an internal engagement feature of outer member 404 is provided by a distal upraised end portion 437 of the restriction 424. As shown in FIG. 3a, when the needle 302 is at the ready position, the arms 410 of the inner member 402 are biased away from each other by the needle passing therebetween such that the distal upraised end portion 437 comes into abutment contact with an internal shoulder 435 at the catheter hub 202 to prevent proximal movement of the needle tip protector relative to the catheter hub 202. As the needle 302 is retracted proximally and its transition 310 comes into contact with the bump washer 414 at the outer member 404, further proximal movement of the needle pulls the distal tip of the needle into the inner member 402 with the arms 410 of the inner member 402 collapsing toward each other due to the sliding surfaces of their respective ramps 432 being biased by the corresponding restrictions 424 at the outer member 404, as per shown in FIG. 3b, such that the distal tip 304 of the needle 302 is non-removably captured in the inner member 402. With the collapsing of the arms 410, the respective distal upraised end portions 437 of the restrictions 424 at the outer member 404 are no longer biased into abutment contact with the internal shoulder 435. As a result, the outer member 404 is no longer in fixed engagement with the catheter hub 202. Further proximal movement of the needle moves the retainer 406 from a first or distal position (FIG. 3a) to a second or proximal position (FIG. 3b) in the proximal chamber 408f of collar 408 to enable the collar 408 and the catheter hub 202 to disengage from each other. FIG. 3d shows the needle tip protector assembly 400 and the catheter hub assembly 200 separated from each other when the distal portion 408a of the collar 408 is disengaged from the proximal end of the catheter hub 202.

With the needle tip protector assembly 400 in the safe position and the inner member 402 in contact with the proximal wall of the outer member 404, further proximal movement of the insertion needle 302 causes the retainer 406, and other components of the needle tip protector assembly 400, to move proximally relative to the collar 408 to a proximal retainer position. This motion causes external engagement features of the retainer 406 to move proximally away from the corresponding outer surfaces of the catheter hub 202, as shown in the progression of movement between FIGS. 3b and 3c. The sliding surface of the outer member 404 is also moved proximally and out of contact with the inner surface of the catheter hub 202, at least in embodiments that include contact between the catheter hub 202 and inner member 402.

The needle tip protector assembly 400 may include a feature that resists proximal movement of the retainer 406 to the proximal release position prior to being in the safe position. The illustrated example embodiment includes a retention finger 450 that is integrated into the enlarged distal portion 408a of collar 408 and that includes a spring arm and a retention tab 442. The retention tab is positioned distally to the main portion of retainer 406. Proximal movement of the retainer 406 is resisted by the retention tab and its finger 450 such that a given force in the proximal direction of moving retainer 406 relative to collar 408 is needed to overcome the resistance provided by the retention tab 442 and its finger 450. In this respect, the retention tab 442 and its finger 450 of the collar 408 provide a release threshold force that is to be overcome prior to the catheter hub assembly 200 being released from the needle tip protection assembly 400.

The release threshold force may be higher than the forces associated with movement from the ready position to the safe position (i.e., the safety threshold force), according to some embodiments. Having the release threshold force higher than the safe threshold force may prevent the catheter from being released prior to the tip protection assembly being moved to the safe position. The release threshold force, according to some embodiments, is more than 2× the safety threshold force, more than 3× the safety threshold force, or more than 5× the safety threshold force.

Figure 3C:
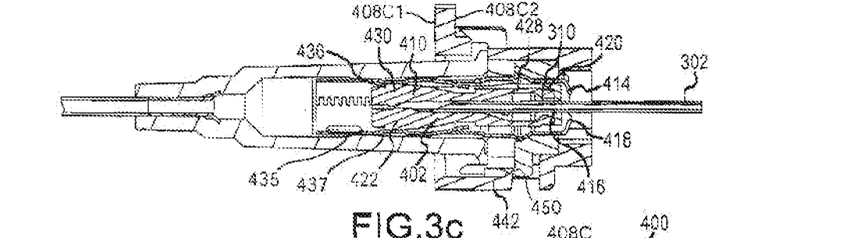
Figure 3D:
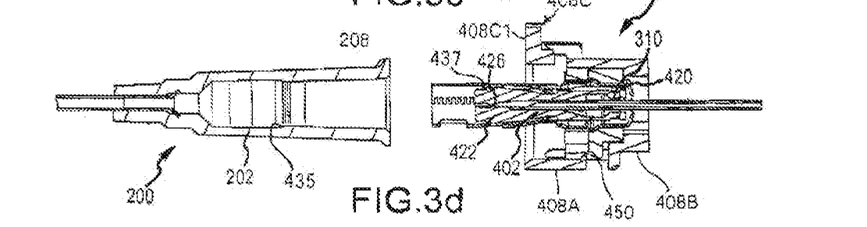
Figure 4A:
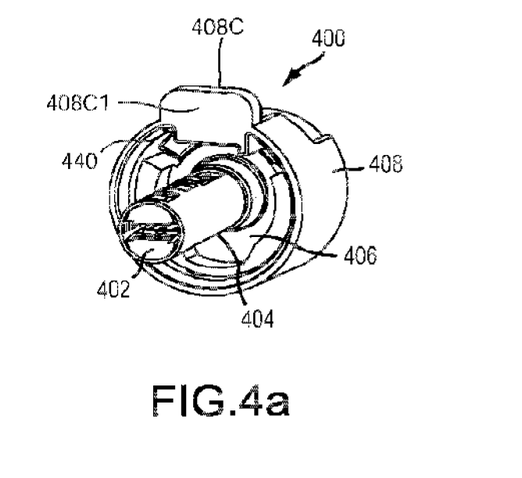
FIGS. 4a-4c are perspective views, taken from a distal vantage, of the tip protector assembly of FIGS. 1a-3d in each of a ready position (FIG. 4a), a safe position (FIG. 4b) and a release position (FIG. 4c). The catheter and needle are removed from FIGS. 4a-4c for purposes of illustration.
Figure 4B:
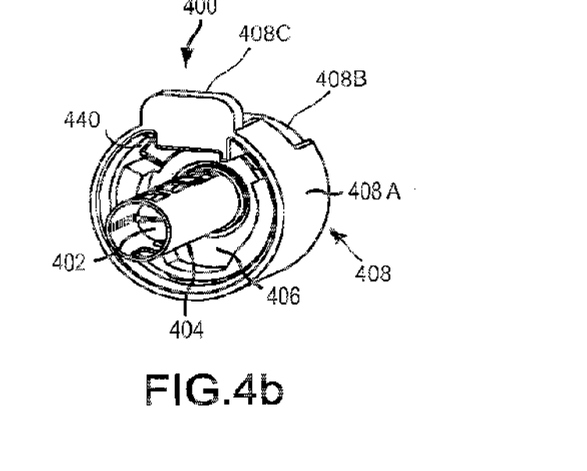
Figure 4C:
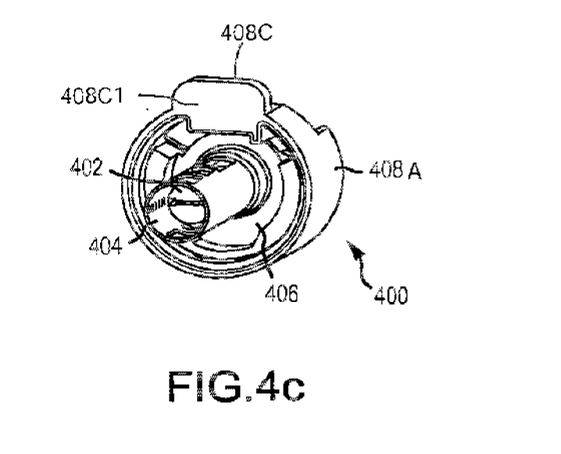
Figures 5, 6, 7, 8:
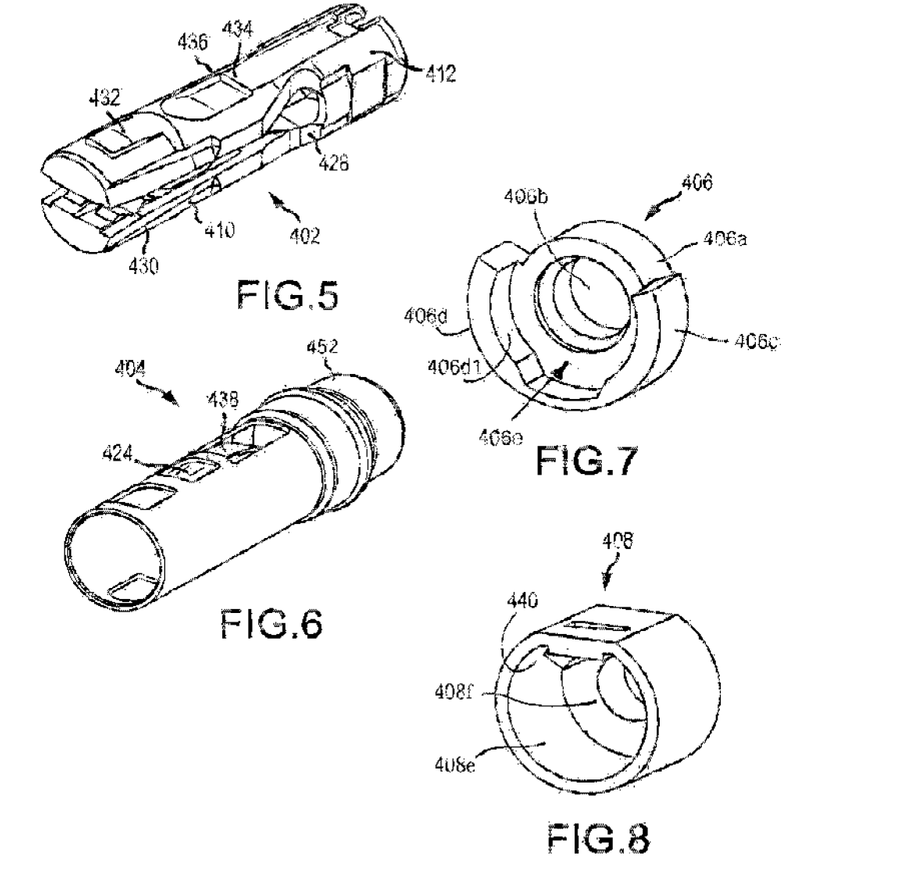
FIG. 5 is a perspective view of an inner member of a tip protector assembly, according to one example embodiment.
FIG. 6 is a perspective view of an outer member of a tip protector assembly, according to one example embodiment.
FIG. 7 is a perspective view of a retainer of a tip protector assembly, according to one example embodiment.
FIG. 8 is a perspective view of another embodiment of the collar of a needle tip protector assembly that does not have an upright.

The catheter hub 202 is released from secure connection to the tip protection assembly 400 when the external engagement features of the retainer 406 are out of engagement with the catheter hub 202, as shown in FIG. 3c. In this position, the further proximal movement of the insertion needle assembly 300 will pull the needle tip protector 400 away from the catheter hub 202, as reflected in FIG. 3d. Separation of the collar 408 from the catheter hub 202 may be accompanied by a slight jogging of the tip protector in a lateral direction, away from the needle passage, according to some embodiments. The sloped shape of the luer lug and/or the notch may promote this motion. Additionally, or alternately, the clinician may tilt pull on the insertion needle assembly at an upward angle to promote separation of the catheter from the collar.

Figure 9:
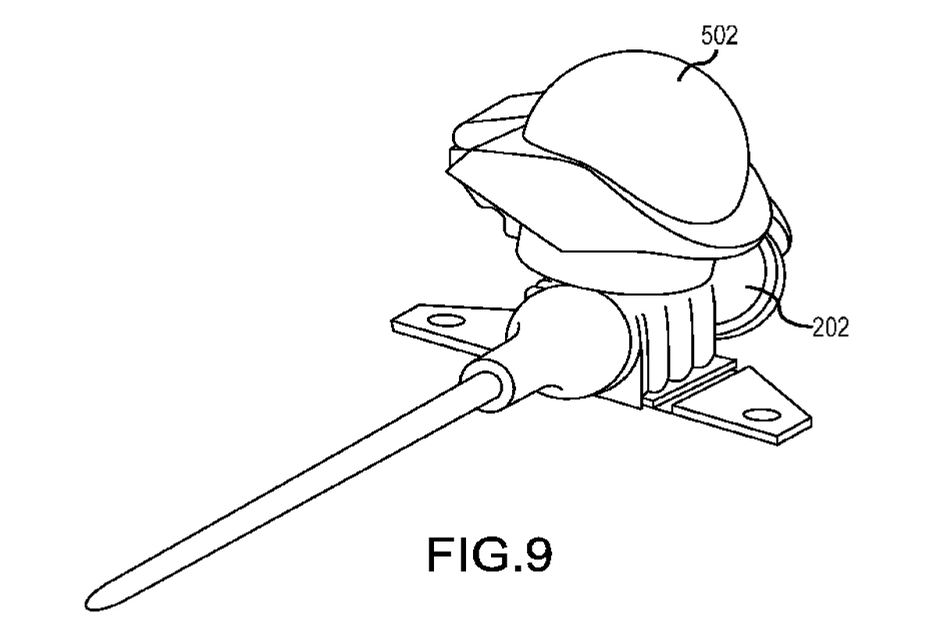
FIG. 9 is a perspective view of a catheter hub assembly that includes a side port.
Figure 10:
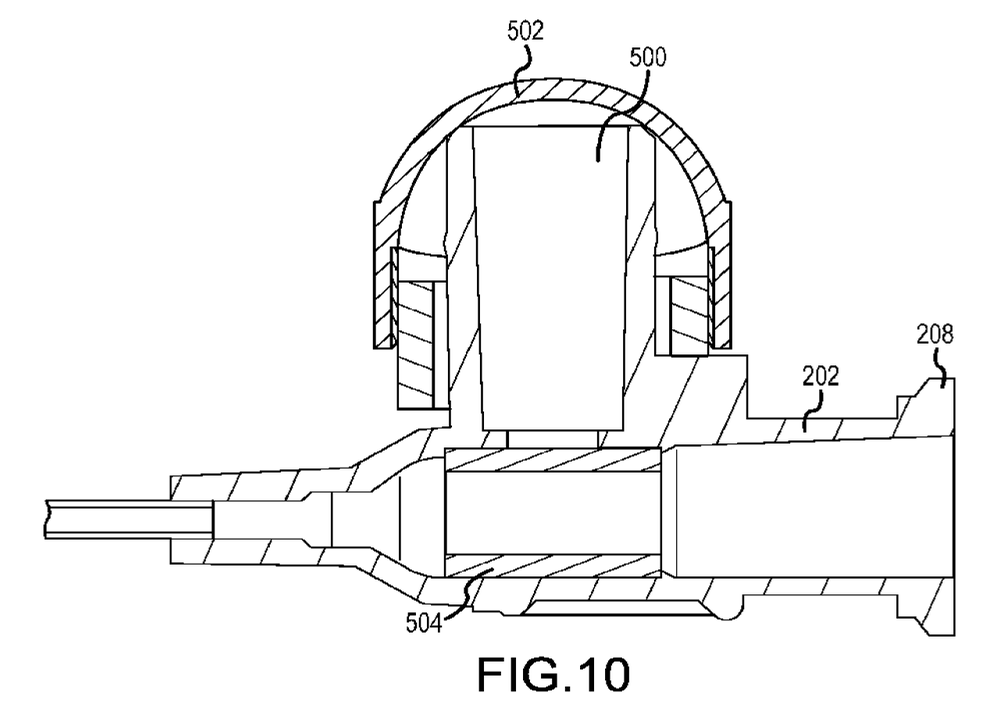
FIG. 10 is a cross sectional view of the catheter hub shown in FIG. 9.

The catheter hub may include a side port 500, such as in the example embodiment of FIGS. 9 and 10. As shown, the catheter hub 202 includes a side port that may be accessed through a lateral, luer type connection that is integrated into the catheter hub. A side port cap 502 may be selectively positioned over the side port to close and open access thereto, as desired. A flexible, cylindrically shaped septum is positioned internally to the catheter hub. The septum 504 is moved away from the side port by pressurized fluid that is introduced into the luer to allow the pressurized fluid to enter the catheter hub. In the absence of pressurized fluid in the luer, the septum closes access to the side port to prevent the escape of fluids from the catheter.

Various example embodiments of catheters are described herein for use in accessing the vein of a subject. It is to be appreciated, however, that the example embodiments described herein may alternately be used to access the vasculature of a subject at locations other than a vein, including but not limited to the artery of a subject. It is additionally to be appreciated that the term "clinician" refers to any individual that may be performing a catheter insertion procedure with any of the example embodiments described herein or combinations thereof. Similarly, the term "subject", as used herein, is to be understood to refer to an individual or object in which a catheter is to be inserted, whether human, animal, or inanimate. Various descriptions are made herein, for the sake of convenience, with respect to procedures being performed by a clinician to access the vein of a subject, while the disclosure is not limited in this respect.

It is also to be appreciated that the term "distal", as used herein, refers to the direction, taking along an axis that lies parallel to the needle of a safety catheter assembly that is closest to a subject during catheter insertion. Conversely, the term "proximal", as used herein, refers the direction lying along the axis parallel to the needle that is farther away from the subject when the catheter is inserted into the vein of the subject—that is, opposite to the distal direction.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more features as variously disclosed or otherwise demonstrated herein.

The invention claimed is:

1. A catheter assembly, comprising:
   a catheter hub having a proximal end and a distal end, an interior cavity defined between the proximal end and the distal end, a side port extending from the catheter hub to enable fluid to pass into the interior cavity from the side port, and a septum positioned in the interior cavity;
   a catheter extending distally from the distal end of the catheter hub;
   a needle having a sharp distal tip and a proximal end extending distally from a needle hub, the needle adapted to slidably extend past the septum and through the catheter hub into the catheter such that the distal tip extends beyond the distal end of the catheter when the catheter assembly is in a ready position;
   a collar having an open distal end and a proximal end positioned between the catheter hub and the needle hub, an upright extending upwardly from a distal portion of the collar, the distal end of the collar opens into a chamber adapted to receive the proximal end of the catheter hub; and
   a needle tip protector at least partially housed in the collar, the needle movable through the needle tip protector between the ready position and a safe position;
   wherein, in the ready position, the proximal end of the catheter hub is in the chamber of the collar and the collar and the catheter hub are in fixed engagement with each other, and
   wherein, in the safe position, the distal tip of the needle is non-removably captured in the needle tip protector.

2. The catheter assembly of claim 1, wherein the needle has a transition proximal the distal tip that interacts with the needle tip protector to move the catheter assembly between the ready and safe positions.

3. The catheter assembly of claim 2, wherein the collar includes a proximal portion having a proximal base, the chamber in the collar separated into a distal chamber and a proximal chamber, the distal chamber having a cross dimension larger than a cross dimension of the proximal chamber, wherein the needle tip protector has a proximal needle stop having an opening adapted to be in contact with the proximal base of the collar and in alignment with an opening at the proximal base, the opening at the proximal needle stop of the needle tip protector preventing the transition of the needle from passing therethrough such that proximal movement of the needle relative to the catheter hub causes the needle tip protector and the collar to move proximally relative to the catheter hub when the transition comes into contact with the proximal needle stop of the needle tip protector.

4. The catheter assembly of claim 3, wherein the proximal needle stop of the needle tip protector is movably retained within the proximal chamber of the collar.

5. The catheter assembly of claim 1, wherein the septum comprises a flexible cylindrical shape.

6. The catheter assembly of claim 1, wherein the upright has a distal front surface that is flush with the distal end of the collar and a proximal back surface.

7. The catheter assembly of claim 1, wherein in the ready position, a proximal portion including the proximal end of the catheter hub is positioned in the distal chamber of the collar.

8. The catheter assembly of claim 3, wherein further movement of the needle after the distal tip of the needle is captured inside the needle tip protector in the safe position enables the collar and the catheter hub to disengage from each other.

9. The catheter assembly of claim 1, further comprising a cap selectively positioned over the external opening to the side port to close and open access to the side port.

10. A catheter assembly, comprising:
a catheter hub having a proximal end and a distal end, an interior cavity defined between the proximal end and the distal end, a side port extending from the catheter hub to enable fluid to pass into the interior cavity from the side port, and a septum positioned in the interior cavity;
a catheter extending distally from the distal end of the catheter hub;
a needle having a sharp distal tip and a proximal end extending distally from a needle hub, the needle adapted to slidably extend past the septum and through the catheter hub into the catheter such that the distal tip extends beyond the distal end of the catheter when the catheter assembly is in a ready position;
a collar having an open distal end and a proximal end positioned between the catheter hub and the needle hub, an upright extending upwardly from a distal portion of the collar, the distal end of the collar opens into a chamber adapted to receive at least the proximal end of the catheter hub, the proximal end of the collar having an opening; and
a needle tip protector having a proximal needle stop housed in the proximal portion of the collar, the needle movable through an opening at the proximal needle stop and the opening at the proximal end of the collar between the ready position and a safe position;
wherein at least the proximal end of the catheter hub is in the chamber of the collar and the collar and the catheter hub are in fixed engagement with each other in the ready position,
wherein the distal tip of the needle is captured in the needle tip protector in the safe position, and
wherein when the catheter hub and the collar are separated from each other, the catheter hub and the collar are in a release position.

11. The catheter assembly of claim 10, wherein the needle has a transition proximal the distal tip that prevents the needle from passing through the opening at the proximal needle stop so that further proximal movement of the needle relative to the catheter hub after the transition of the needle contacts the proximal needle stop causes the proximal needle stop to move the proximal end of the collar proximally relative to the catheter hub to separate the collar from the catheter hub.

12. The catheter assembly of claim 10, wherein the upright has a distal front surface flush with the distal end of the collar and a proximal back surface.

13. The catheter assembly of claim 10, wherein a proximal portion of the catheter hub is positioned in the distal chamber of the collar in the ready position.

14. A method of making a catheter assembly, comprising the steps of:
providing a catheter hub having a proximal end and a distal end, and an interior cavity defined between the proximal end and the distal end;
integrally extending a side port from the catheter hub to enable fluid to enter the interior cavity from the side port;
positioning a septum in the interior cavity of the catheter hub;
extending a catheter from the distal end of the catheter hub;
extending a needle having a sharp distal tip distally from a needle hub, the needle adapted to slidably extend past the septum and through the catheter hub into the catheter such that the distal tip extends beyond the distal end of the catheter when the safety catheter assembly is in a ready position;
positioning a collar having an open distal end and a proximal end between the catheter hub and the needle hub, the collar having a distal portion and a proximal portion, the distal end of the collar opens into a distal chamber and a proximal chamber, the distal chamber adapted to receive at least the proximal end of the catheter hub;
extending an upright upwardly from the distal portion of the collar; and
at least partially housing a needle tip protector in the collar such that the needle is movable through the needle tip protector between the ready position and a safe position wherein the distal tip of the needle is captured in the needle tip protector.

15. The method of claim 14, further comprising the step of:
forming a transition at the needle proximal the distal tip of the needle such that the transition is adapted to interact with the needle tip protector to move the catheter assembly between the ready and safe positions.

16. The method of claim 15, wherein the distal chamber has a cross dimension larger than a cross dimension of the proximal chamber, the method further comprising the steps of:
configuring the proximal portion of the collar to have a proximal base having an opening;
configuring the needle tip protector to have a proximal needle stop having an opening that prevents the transition of the needle from passing therethrough, the proximal needle stop of the needle tip protector adapted to be in contact with the proximal base of the collar such that proximal movement of the needle relative to the catheter hub causes the needle tip protector and the collar to move proximally relative to the catheter hub when the transition comes into contact with the proximal needle stop.

17. The method of claim 14, wherein the extending the upright step further comprises extending the upright upwardly from the collar with its distal front surface flush with the distal end of the collar.

18. The method of claim 14, further comprising the step of:
   positioning a proximal portion of the catheter hub in the distal chamber of the collar in the ready position.

19. The method of claim 16, wherein after the distal tip of the needle is captured inside the needle tip protector, the method further comprising a release position step of:
   moving the needle further proximally relative to the catheter hub to enable the collar and the catheter hub to separate from each other.

\* \* \* \* \*